US008698886B2

(12) United States Patent
 Hirakawa (10) Patent No.: US 8,698,886 B2
(45) Date of Patent: Apr. 15, 2014

(54) APPARATUS FOR ESTIMATING SHAPE OF INSERTION PORTION

(71) Applicant: Olympus Medical Systems Corp., Tokyo (JP)

(72) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/750,637

(22) Filed: Jan. 25, 2013

(65) Prior Publication Data

US 2013/0201311 A1  Aug. 8, 2013

Related U.S. Application Data

(63) Continuation of application No. PCT/JP2012/060368, filed on Apr. 17, 2012.

(30) Foreign Application Priority Data

Aug. 1, 2011 (JP) ................................. 2011-168607

(51) Int. Cl.
 *A61B 1/04* (2006.01)
(52) U.S. Cl.
 USPC ............................................................ 348/74
(58) Field of Classification Search
 USPC .................................................... 348/65, 74
 See application file for complete search history.

(56) References Cited

U.S. PATENT DOCUMENTS

| 8,243,130 | B2 * | 8/2012 | Kawano | 348/74 |
| 8,376,934 | B2 * | 2/2013 | Takahashi et al. | 600/106 |
| 8,523,765 | B2 * | 9/2013 | Kawai | 600/141 |
| 2003/0191367 | A1 * | 10/2003 | Belson et al. | 600/146 |
| 2008/0221592 | A1 * | 9/2008 | Kawai | 606/130 |
| 2011/0098533 | A1 * | 4/2011 | Onoda et al. | 600/117 |
| 2011/0105957 | A1 * | 5/2011 | Kourogi et al. | 600/595 |
| 2011/0292196 | A1 * | 12/2011 | Kawano | 348/74 |

FOREIGN PATENT DOCUMENTS

| JP | A-11-19027 | 1/1999 |
| JP | A-2006-314775 | 11/2006 |
| JP | A-2007-151862 | 6/2007 |
| JP | A-2010-104426 | 5/2010 |
| JP | A-2011-59020 | 3/2011 |
| JP | A-2011-104053 | 6/2011 |
| JP | A-2012-509715 | 4/2012 |
| WO | WO 2010/060039 A2 | 5/2010 |

OTHER PUBLICATIONS

Jun. 26, 2012 International Search Report issued in International Application No. PCT/JP2012/060368 (with translation).

* cited by examiner

*Primary Examiner* — Sath V Perungavoor
*Assistant Examiner* — James Pontius
(74) *Attorney, Agent, or Firm* — Oliff PLC (57) ABSTRACT

An apparatus for estimating a shape of an insertion portion includes an insertion portion, an acceleration calculation unit calculating acceleration at measurement points, and a determination unit which determines whether the measurement points move. The apparatus further includes an attitude information calculation unit calculating attitude information of the measurement points in a resting state, an attitude estimation unit estimating a movement period attitude, a movement vector calculation unit calculating a movement vector of the measurement points, and a position calculation unit calculating a position of the measurement points. The apparatus further includes an image generation unit generating a display image expressing the position and the movement vector.

8 Claims, 6 Drawing Sheets

APPARATUS FOR ESTIMATING SHAPE OF INSERTION PORTION

CROSS-REFERENCE TO RELATED APPLICATIONS

This application is a Continuation Application of PCT Application No. PCT/JP2012/060368, filed Apr. 17, 2012 and based upon and claiming the benefit of priority from prior Japanese Patent Application No. 2011-168607, filed Aug. 1, 2011, the entire contents of all of which are incorporated herein by reference.

BACKGROUND OF THE INVENTION

1. Field of the Invention

The present invention relates to an apparatus for estimating a shape of an insertion portion.

2. Description of the Related Art

In general, a method of detecting an attitude or movement of an object by using an inertia sensor, or the like is known. According to the method, a plurality of sensors is arranged in a transformed object to estimate a shape of the object in a resting state.

For example, in Jpn. Pat. Appln. KOKAI Publication NO. 2007-151862, a technology regarding an endoscope in which acceleration sensors are disposed is disclosed. In the endoscope, an attitude of a part in which the acceleration sensor is disposed is detected based on an output of the acceleration sensor. Further, a displacement of the part in which the acceleration sensor is disposed is detected by integrating the output of the acceleration sensor.

Further, in Jpn. Pat. Appln. KOKAI Publication NO. 2011-059020, a technology regarding a 3D attitude estimation device is disclosed. The 3D attitude estimation device includes an acceleration sensor and an attitude angle estimation unit estimating a 3D attitude angle. Jpn. Pat. Appln. KOKAI Publication NO. 2011-059020 discloses a technology that measures acceleration depending on movement with high precision by removing a gravity acceleration component from acceleration detected by the acceleration sensor based on an attitude angle estimated by the attitude angle estimation unit.

BRIEF SUMMARY OF THE INVENTION

According to an aspect of the invention, an apparatus for estimating a shape of an insertion portion includes an insertion portion configured to be transformed; an acceleration calculation unit configured to calculate acceleration at each of a plurality of measurement points set in the insertion portion; a determination unit configured to determine whether the measurement points move, based on the acceleration calculated by the acceleration calculation unit; an attitude information calculation unit configured to calculate first attitude information of each of the measurement points in a resting state before a movement period when the determination unit determines that the measurement points moves and second attitude information of each of the measurement points in a resting state after the movement period; an attitude estimation unit configured to estimate a movement period attitude which is an attitude of each of the measurement points during the movement period, based on the first attitude information and the second attitude information calculated by the attitude information calculation unit; a movement vector calculation unit configured to correct the acceleration during the movement period calculated by the acceleration calculation unit, based on the movement period attitude of the measurement points estimated by the attitude estimation unit and to calculate a movement vector which indicates a movement direction and a movement amount of each of the measurement points during the movement period, based on the corrected acceleration; a position calculation unit configured to calculate a position of each of the measurement points based on the first attitude information or the second attitude information of the measurement points calculated by the attitude information calculation unit; and an image generation unit configured to generate and to output a display image expressing the position of each of the measurement points calculated by the position calculation unit and the movement vector calculated by the movement vector calculation unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
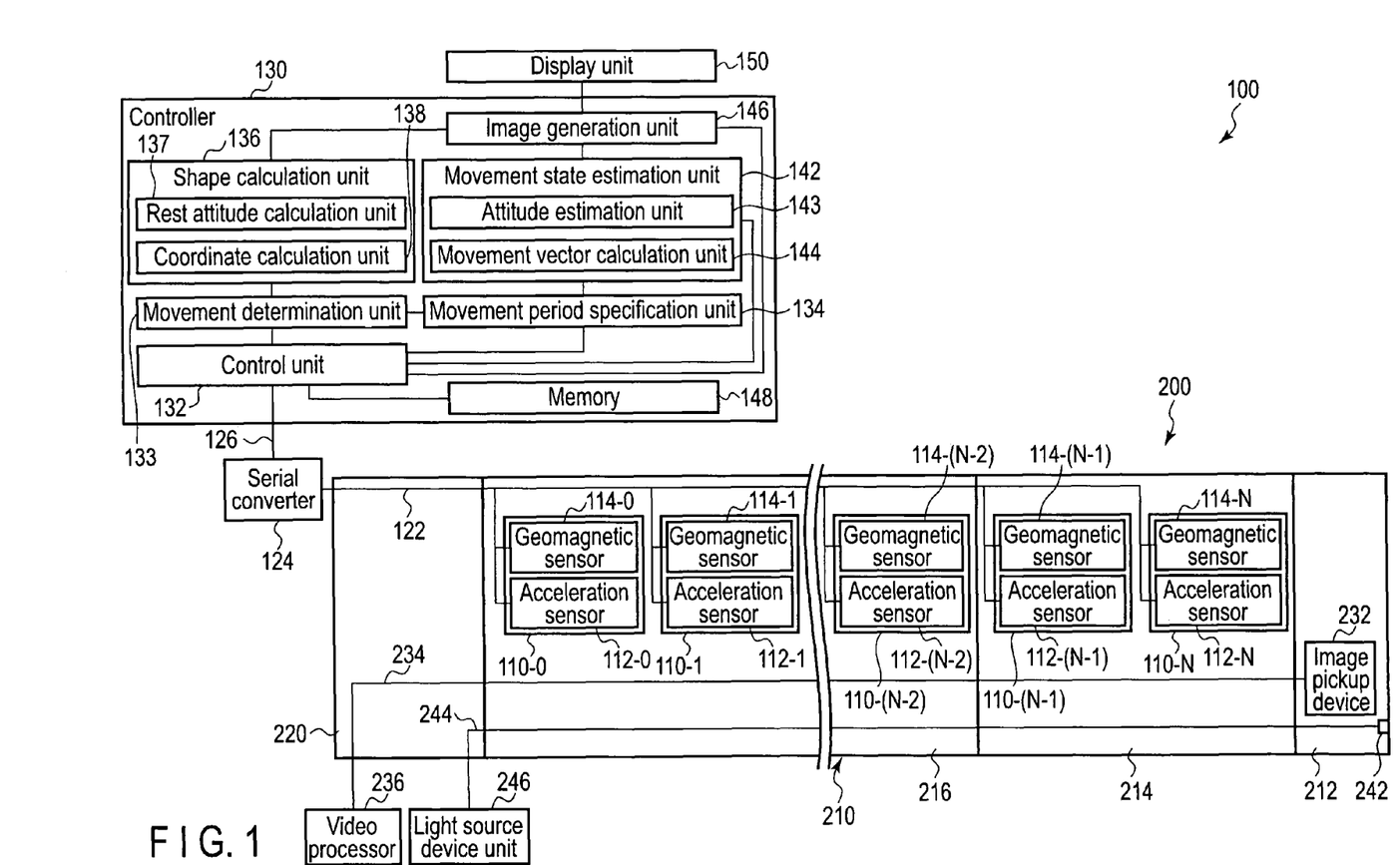
FIG. 1 is a block diagram illustrating a configuration example of an apparatus for displaying a shape of an insertion portion according to an embodiment of the present invention.

Embodiments of the present invention will be described with reference to the accompanying drawings. An overview of a configuration of an apparatus for displaying a shape of an insertion portion according to an embodiment of the present invention is illustrated in FIG. 1. In this embodiment, a case in which the apparatus for displaying a shape of an insertion portion is applied to display the shape of the insertion portion of an endoscope is described as an example. As illustrated in FIG. 1, an apparatus for displaying a shape of an insertion portion 100 is configured by using a general endoscope 200.

The endoscope 200 includes an insertion portion 210 having an elongate shape which is inserted into a body cavity and an operation unit 220 provided at a proximal end side of the insertion portion 210. The insertion portion 210 includes a distal end rigid portion 212 provided at the most distal end, a bending portion 214 provided at a proximal end side of the distal end rigid portion 212, and an elongate flexible tube 216 provided at a proximal end side of the bending portion 214.

An image pickup device 232 such as a CCD, or the like which is used to pick up a subject is provided at the distal end rigid portion 212. One end of an image pickup signal line 234 is connected to the image pickup device 232. The other end of the image pickup signal line 234 is extended to the outside of the endoscope 200 from the operation unit 220 through the inside of the insertion portion 210. The other end of the image pickup signal line 234 is connected to a video processor 236 which is an image processing unit.

Further, an irradiation window 242 for irradiating illumination to the subject is provided at the distal end rigid portion 212. One end of a light guide 244 is connected to the irradiation window 242. The other end of the light guide 244 is extended to the outside of the endoscope 200 from the operation unit 220 through the inside of the insertion portion 210. The other end of the light guide 244 is connected to a light source unit 246.

Further, four bending operation wires (not illustrated) pass through the inside of the flexible tube 216. One end of each of four bending operation wires is connected to a distal end of the bending portion 214 of the insertion portion 210. The other end of the bending operation wire is connected to a bending operation knob (not illustrated) which is a bending operation unit provided in the operation unit 220. The bending operation wire moves in a longitudinal direction by operating the bending operation knob. The bending portion 214 is bent in four directions of upper, lower, left, and right directions by moving the bending operation wire.

A plurality of sensor units 110 is provided at the insertion portion 210 along a longitudinal axis of the insertion portion 210. In this embodiment, the number of sensor units 110 is set as N+1. Units will be called sensor units 110-0 to 110-N, sequentially from a 0-th sensor unit provided at the most proximal end side of the insertion portion 210 to an N-th sensor unit at the most distal end side of the insertion portion 210.

Respective sensor units 110-$i$ ($i$=0, 1, 2, . . . , N) are disposed at measurement points which are spaced apart from each other in a longitudinal direction by a predetermined interval l. The interval l is, for example, 50 mm. In this embodiment, the respective sensor units 110-$i$ are arranged at the predetermined interval l, but the present invention is not limited thereto, and the respective sensor units may be arranged at different predetermined intervals. Herein, for example, the sensor unit 110-0 at the most proximal end side is disposed at a proximal end of the flexible tube 216, and the sensor unit 110-N at the most distal end side is disposed at a distal end of the bending portion 214.

Each sensor unit 110 includes an acceleration sensor 112 measuring acceleration and a geomagnetic sensor 114 measuring geomagnetism. Herein, sensors of the sensor unit 110-$i$ will be referred to as an acceleration sensor 112-$i$ and a geomagnetic sensor 114-$i$.

A serial bus 122 such as an I2C is connected to the acceleration sensor 112-$i$ and the geomagnetic sensor 114-$i$ of each sensor unit 110-$i$. The serial bus 122 is extended to the outside of the endoscope 200 from the operation unit 220 through the inside of the insertion portion 210. A proximal end of the serial bus 122 is connected to a serial converter 124. The serial converter 124 converts a serial signal of measurement data input through the serial bus 122 from each sensor unit 110-$i$ into, for example, a USB signal.

One end of a USB cable 126 is connected to the serial converter 124. The other end of the USB cable 126 is connected to a controller 130. A USB signal of data measured in each sensor unit 110-$i$ is input into the controller 130 from the serial converter 124. The controller 130 may be, for example, a personal computer or a dedicated calculator. Further, for example, a display unit 150 which is a display is connected to the controller 130.

The controller 130 includes a control unit 132, a movement determination unit 133, a movement period specification unit 134, a shape calculation unit 136, a movement state estimation unit 142, an image generation unit 146, and a memory 148. The control unit 132 controls an operation of each unit of the controller 130. The movement determination unit 133 determines whether the sensor unit 110 is in a movement state, based on data of an acceleration input from the acceleration sensor 112-$i$ of each sensor unit 110-$i$. When the movement determination unit 133 determines that the sensor unit 110 is in the movement state, the movement period specification unit 134 specifies a movement period during which the sensor unit 110 is in the movement state.

The shape calculation unit 136 performs a rest shape calculation processing in order to calculate the shape of the insertion portion 210 in a resting state. The shape calculation unit 136 includes a rest attitude calculation unit 137 and a coordinate calculation unit 138. The rest attitude calculation unit 137 calculates an attitude of each sensor unit 110 based on outputs of the acceleration sensor 112 and the geomagnetic sensor 114. The coordinate calculation unit 138 calculates a coordinate in which each sensor unit 110 is positioned, that is, a relative position of each sensor unit 110 to each of other sensor units 110, based on the attitude of each sensor unit 110 calculated by the rest attitude calculation unit 137.

The movement state estimation unit 142 performs a movement state calculation processing in order to calculate a state of the insertion portion 210 in the movement state. The movement state estimation unit 142 includes an attitude estimation unit 143 and a movement vector calculation unit 144. The attitude estimation unit 143 calculates the attitude of each sensor unit 110 at each time of the movement period specified by the movement period specification unit 134, based on the attitude of each sensor unit in the resting state. The movement vector calculation unit 144 corrects the acceleration which is the output of each acceleration sensor 112, based on the attitude of each sensor unit 110 calculated by the attitude estimation unit 143. The movement vector calculation unit 144 calculates a movement vector of each sensor unit 110 in the movement state, based on the corrected acceleration.

The image generation unit 146 prepares an image to express a position coordinate and a movement vector, based on the position coordinate of each sensor unit 110 calculated by the shape calculation unit 136 and the movement vector of each sensor unit 110 in the movement state, which is calculated by the movement state estimation unit 142. The image generation unit 146 displays the prepared image on the display unit 150. The memory 148 stores the output of each sensor unit 110 or a calculation result of each unit. Further, the memory 148 stores various programs and the like required for processing. The display unit 150 displays the image based on an instruction of the image generation unit 146.

Like this, for example, the insertion portion 210 functions as an insertion portion configured to be transformed. For example, the sensor unit 110 functions as an attitude acquisition unit that acquires the acceleration applied to the measurement point and attitude information regarding the attitude of each measurement point in the resting state. For example, the shape calculation unit 136 functions as a shape calculation unit that calculates the attitude of each measurement point and a relative position to other measurement points, based on the position of each measurement point in the insertion portion and each of attitude information. For example, the movement determination unit 133 functions as a movement determination unit that determines whether the measurement point moves based on the acceleration. For example, the movement period specification unit 134 functions as a movement period specification unit that specifies the movement period when the movement point moves, based on the determination. For example, the attitude estimation unit 143 functions as an attitude estimation unit that estimates a movement period attitude which is the attitude of each measurement point during the movement period, based on each measurement point in the resting state before and after the movement period. For example, the movement vector calculation unit 144 functions as a movement vector calculation unit that calculates the movement vector of each measurement point during the movement period, based on each acceleration corrected according to each movement period attitude. For example, the image generation unit 146 functions as an image generation unit that generates a display image indicating each relative position and each movement vector. For example, the display unit 150 functions as a display unit that displays the display image.

Figure 2:
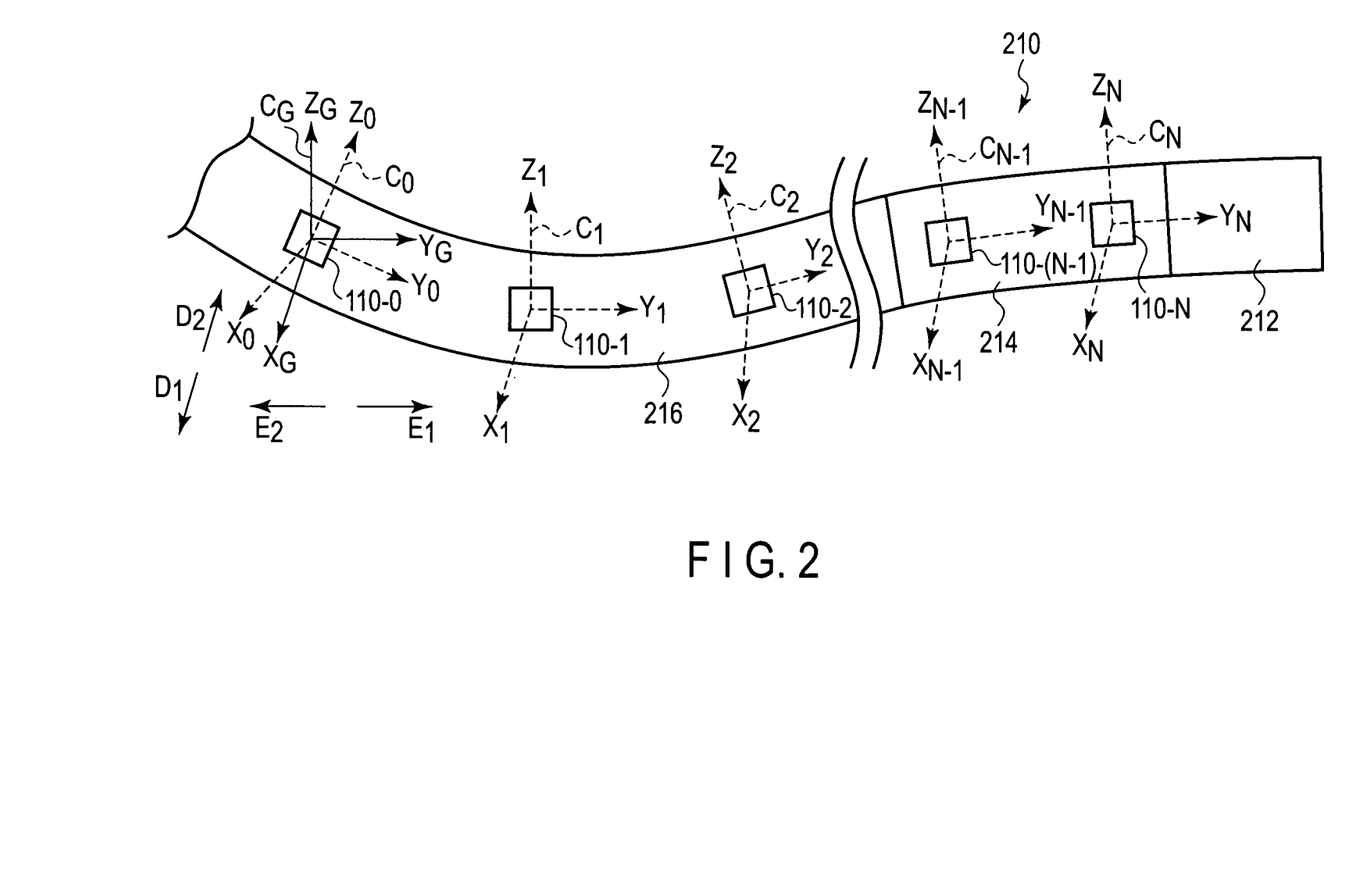
FIG. 2 is a diagram for describing various coordinates according to the embodiment of the present invention.

Herein, a coordinate system used in this embodiment will be described with reference to FIG. 2. The insertion portion 210 of the endoscope 200 is illustrated in FIG. 2. In this embodiment, a global coordinate system $C_G$ which is a right-handed orthogonal Cartesian coordinate system having an $X_G$ axis, a $Y_G$ axis, and a $Z_G$ axis is defined by setting the center of the sensor unit 110-0 at the most proximal end side as an original point. Each coordinate axis of the global coordinate system $C_G$ is represented by a solid line in FIG. 3. Herein, the $X_G$ axis represents a predetermined direction perpendicular to a vertical direction in which gravity acts. In this embodiment, the $X_G$ axis is parallel to arrows D1 and D2 of FIG. 2, and the direction of the arrow D1 is a positive direction. The present invention is not limited thereto, but the positive direction of the $X_G$ axis of the global coordinate system $C_G$ is set as a magnetic north direction in this embodiment. The $Y_G$ axis is perpendicular to the vertical direction and further, perpendicular to the $X_G$ axis direction. In this embodiment, the $Y_G$ axis is parallel to arrows E1 and E2, and the direction of the arrow E1 is a positive direction. The $Z_G$ axis is set as the vertical direction, and an upper vertical direction is set as a positive direction. The global coordinate system $C_G$ does not rotate with respect to the vertical direction and the magnetic north direction, but moves in parallel with the movement of the insertion portion 210.

Further, as illustrated in FIG. 2, a local coordinate system $C_{Bi}$ which is a right-handed orthogonal Cartesian coordinate system having $X_{Bi}$, $Y_{Bi}$, and $Z_{Bi}$ axes by setting the center of the sensor unit 110-i as the original point is defined in each sensor unit 110-i. Each coordinate axis of each local coordinate system $C_{Bi}$ is represented by a dashed line in FIG. 2. Herein, the $X_{Bi}$ axis coincides with a left-right direction defined in the endoscope 200 and is an axis in which a right direction of the endoscope 200 is a positive direction when the distal end side is viewed from the proximal end side. The $Y_{Bi}$ axis coincides with a longitudinal direction of the endoscope 200 and is an axis in which a distal end direction is a positive direction. The $Z_{Bi}$ axis coincides with a up-down direction defined in the endoscope 200 and is an axis in which an upper direction of the endoscope 200 is set as a positive direction.

The original of each local coordinate system $C_{Bi}$ moves in parallel to the global coordinate system $C_G$. In addition, each local coordinate system $C_{Bi}$ rotates at $\alpha_i$ on the periphery the $X_G$ axis, at $\beta_i$ on the periphery the $Y_G$ axis, and at $\gamma_i$ on the periphery of the $Z_G$ axis, with respect to the global coordinate system $C_G$. Herein, $\alpha_i$, $\beta_i$, and $\gamma_i$ will be referred to as a pitch angle, a roll angle, and a yaw angle, respectively. Further, three angles of the pitch angle $\alpha_i$, the roll angle $\beta_i$, and the yaw angle $\gamma_i$ will be collectively referred to as attitude angles. In the attitude angles of $\alpha_i$, $\beta_i$, and $\gamma_i$, a clockwise direction is set as a positive direction when viewed from a negative direction of the $X_G$ axis, the $Y_G$ axis, and the $Z_G$ axis, respectively.

Each acceleration sensor 112-i measures an $X_{Bi}$ axis direction-component, a $Y_{Bi}$ axis direction-component, and a $Z_{Bi}$ axis direction-component of acceleration at the original point of the local coordinate system $C_{Bi}$. Further, each geomagnetic sensor 114-i measures an $X_{Bi}$ axis direction-component, a $Y_{Bi}$ axis direction-component, and a $Z_{Bi}$ axis direction-component of the geomagnetism at the original point of the local coordinate system $C_{Bi}$. The attitude of the sensor unit 110-i is detected by calculating values of the attitude angles $\alpha_i$, $\beta_i$, and $\gamma_i$, based on the each acceleration sensor 112-i and each geomagnetic sensor 114-i.

Figure 3:
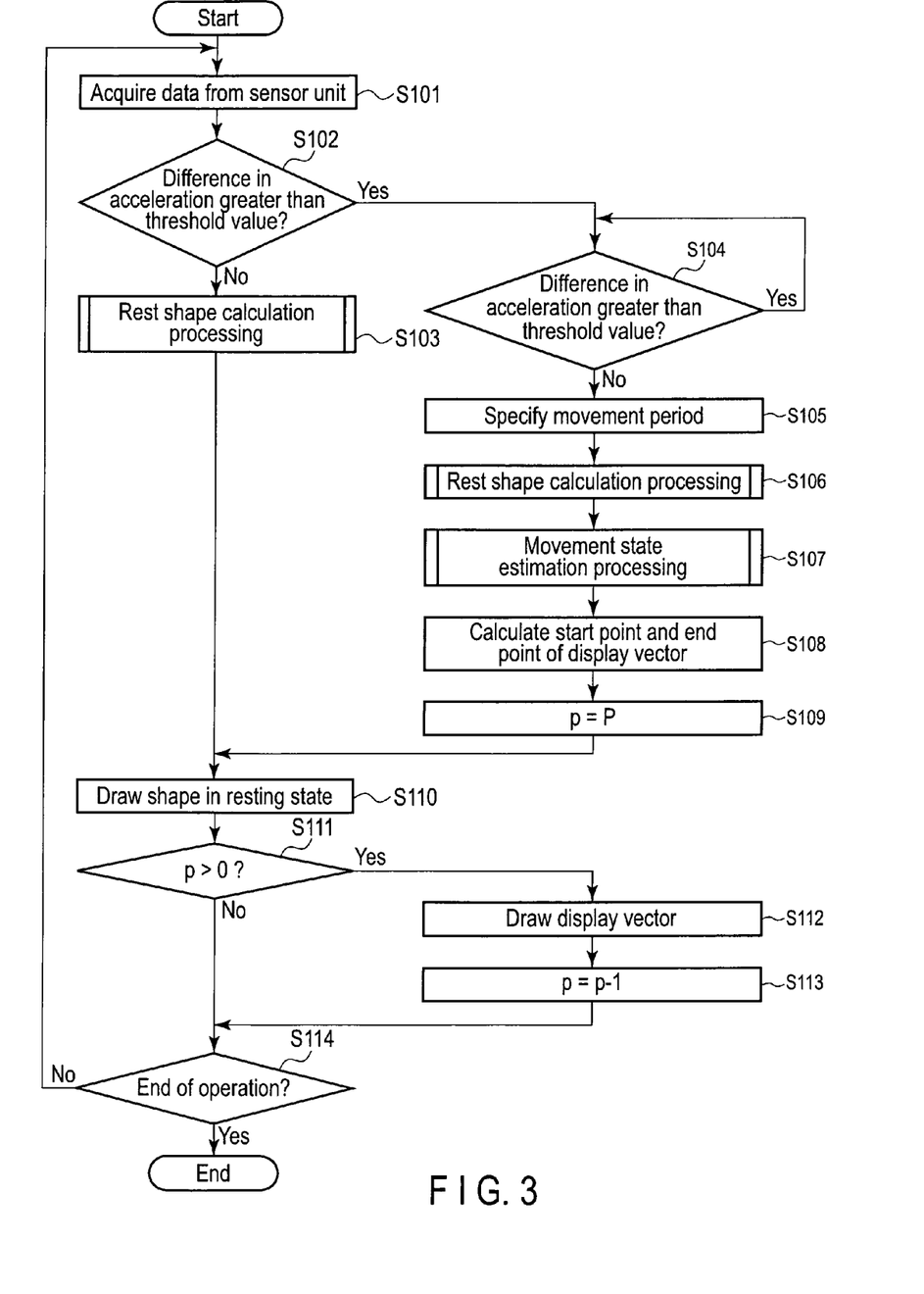
FIG. 3 is a flowchart illustrating a processing example of the apparatus for displaying a shape of an insertion portion according to the embodiment of the present invention.

Next, an operation of the apparatus for displaying a shape of an insertion portion 100 according to the embodiment will be described. A flowchart of processing by the controller 130 is illustrated in FIG. 3. In step S101, the control unit 132 of the controller 130 acquires data from each sensor unit 110-i. The data includes an output of each acceleration sensor 112-i and an output of each geomagnetic sensor 114-i. The processing illustrated in FIG. 3 is a loop processing repeated until the operation of the apparatus for displaying a shape of an insertion portion 100 is terminated. Therefore, the control unit 132 periodically acquires data from each sensor unit 110-i. The acquired data is stored in the memory 148.

In step S102, the movement determination unit 133 of the controller 130 determines whether a difference between a previously acquired output value and a currently acquired value of an output of any one acceleration sensor 112 is larger than a predetermined threshold value. When differences of outputs of all acceleration sensors 112 are less than or equal to the predetermined threshold value, it is determined that the insertion portion 210 stops. This state will be referred to as a resting state. Further, when a difference regarding an output of any one acceleration sensor 112 is larger than the predetermined threshold value, it is determined that the insertion portion 210 moves. This state will be referred to as a movement state. In the determination, when the differences regarding the outputs of all of the acceleration sensors 112 are less than or equal to the predetermined threshold value, that is, in the resting state, the process proceeds to step S103.

Figure 4:
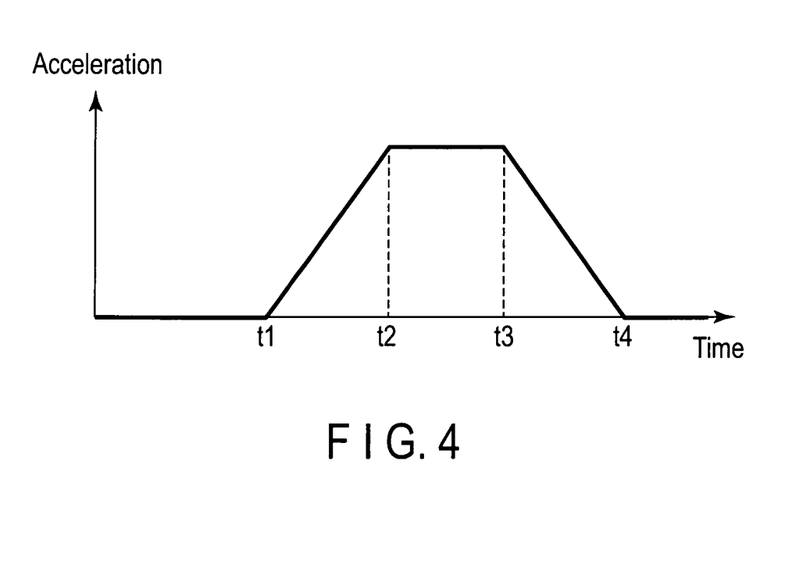
FIG. 4 is a diagram illustrating one example of an acceleration of a sensor unit versus time.

In describing the embodiment, a situation illustrated in FIG. 4 is considered as an example. This figure schematically illustrates a representative value of the output of the acceleration sensor 112. As illustrated in the figure, it is assumed that the output of the acceleration sensor 112 is less than or equal to the predetermined threshold value, that is, in the resting state during a period up to a time t1. During a period from the time t1 to a time t4, it is assumed that the insertion portion 210 is in the movement state in which the output of the acceleration sensor 112 is greater than the predetermined threshold value. After the time t4, it is assumed that the output of the acceleration sensor 112 is less than or equal to the predetermined threshold value, that is, in the resting state. For example, when the time of t<t1 or t>t4, the process proceeds to step S103.

In step S103, the shape calculation unit 136 of the controller 130 performs a rest shape calculation processing. The rest shape calculation processing will be described with reference to a flowchart illustrated in FIG. 5. In step S201, the rest attitude calculation unit 137 in the shape calculation unit 136 calculates a pitch angle $\alpha_i$ and a roll angle $\beta_i$, based on the output of each acceleration sensor 112-$i$. A calculation method of the pitch angle $\alpha_i$ and the roll angle $\beta_i$ will be described.

Figure 5:
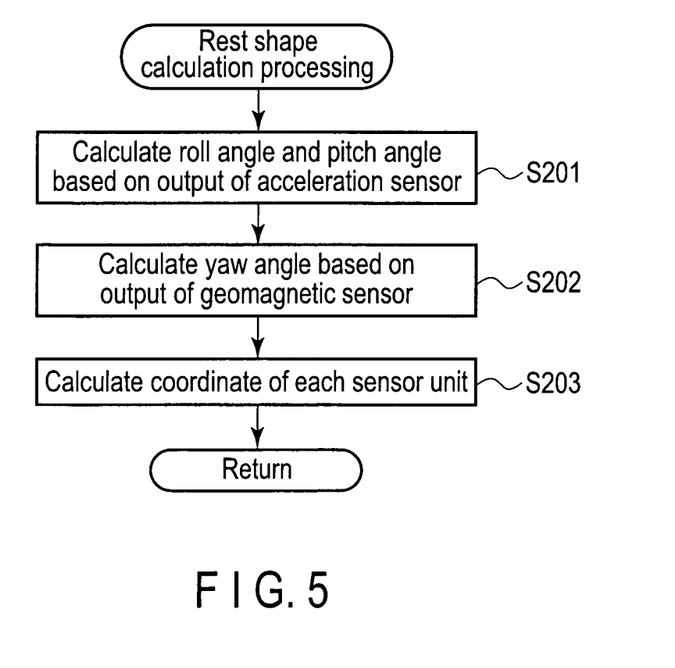
FIG. 5 is a flowchart illustrating a rest shape calculation processing of the apparatus for displaying a shape of an insertion portion according to the embodiment of the present invention.

Attitude angles $\alpha_i$, $\beta_i$, and $\gamma_i$ are assumed as a (Z, X, Y) type which rotates in the order of the yaw angle $\gamma_i$, the pitch angle $\alpha_i$, and the roll angle $\beta_i$. Therefore, a rotation matrix from the global coordinate system $C_G$ to the local coordinate system $C_{Bi}$ is represented by Equation 1 below.

$$C_{Bi}^G = R_{Zi} R_{Xi} R_{Yi} \quad (1)$$

$$= \begin{bmatrix} \cos\gamma_i & -\sin\gamma_i & 0 \\ \sin\gamma_i & \cos\gamma_i & 0 \\ 0 & 0 & 1 \end{bmatrix} \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix}$$

$$= \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_i \cdot \sin\beta_i + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_i & \sin\alpha_i & \cos\alpha_i \cdot \cos\beta_i \end{bmatrix}$$

In the resting state in which the insertion portion 210 stops, only gravity acceleration acts in a lower vertical direction as acceleration. Therefore, in the resting state, an $X_G$ axis direction component, a $Y_G$ axis direction component, and a $Z_G$ axis direction component of an acceleration vector $a_{Gth}$ in the global coordinate system $C_G$ may be represented by Equation 2 below.

$$a_{Gth} = [0\ 0\ -g]^T \quad (2)$$

An acceleration vector $a^t_{obsi}$ measured by each acceleration sensor 112-$i$ at the time t, that is, an $X_{Bi}$ axis direction-component, a $Y_{Bi}$ axis direction-component, and a $Z_{Bi}$ axis direction-component in the local coordinate system $C_{Bi}$ of acceleration will be represented by Equation 3 below.

$$a_{obsi}^t = [a_{Bi\_X}^t\ a_{Bi\_Y}^t\ a_{Bi\_Z}^t]^T \quad (3)$$

In this case, since the local coordinate system $C_{Bi}$ is a coordinate system in which the global coordinate system $C_G$ rotates in the order of the yaw angle $\gamma_i$, the pitch angle $\alpha_i$, and the roll angle $\beta_i$, the acceleration vector $a^t_{obsi}$ observed in the local coordinate system CBi is represented by Equation 4 below.

$$a_{obsi}^t = \begin{bmatrix} a_{Bi\_X}^t \\ a_{Bi\_Y}^t \\ a_{Bi\_Z}^t \end{bmatrix} = (C_{Bi}^G)^T a_{Gth} = -g \begin{bmatrix} -\cos\alpha_i^t \cdot \sin\beta_i^t \\ \sin\alpha_i^t \\ \cos\alpha_i^t \cdot \cos\beta_i^t \end{bmatrix} \quad (4)$$

Herein, by adding a square of a first equation of Equation 4 to a square of a third equation of Equation 4, Equation 5 below is acquired.

$$g\cos\alpha_i^t = \sqrt{a_{Bi\_X}^{t\,2} + a_{Bi\_Z}^{t\,2}} \quad (5)$$

By dividing the second equation of Equation 4 by Equation 5, Equation 6 below is acquired.

$$\alpha_i^t = \tan^{-1}\left(\frac{-a_{Bi\_Y}^t}{\sqrt{a_{Bi\_X}^{t\,2} + a_{Bi\_Z}^{t\,2}}}\right) \quad (6)$$

In this way, a pitch angle $\alpha_i^t$ at each time t of each local coordinate system $C_{Bi}$ is acquired.

Further, by dividing the first equation of Equation 4 by a third equation of Equation 4, Equation 7 below is acquired.

$$\beta_i^t = \tan^{-1}\left(\frac{-a_{Bi\_X}^t}{\sqrt{a_{Bi\_Z}^t}}\right) \quad (7)$$

In this way, a roll angle $\beta_i^t$ at each time t of each local coordinate system $C_{Bi}$ is acquired.

By this configuration, the pitch angle $\alpha_i^t$ and the roll angle $\beta_i^t$ of each sensor unit 110-$i$, that is, each local coordinate system $C_{Bi}$ are calculated, based on the data measured by each acceleration sensor 112-$i$ with respect to each time t.

Referring back to FIG. 5, the description is continued. In step S202, the rest attitude calculation unit 137 calculates the yaw angle $\gamma_i^t$ based on the output of the geomagnetic sensor 114. A calculation method of the yaw angle $\gamma_i^t$ will be described. A geomagnetic vector $m^t_{obsi}$ measured by the geomagnetic sensor 114-$i$ at the time t, that is, an $X_{Bi}$ axis direction-component, a $Y_{Bi}$ axis direction-component, and a $Z_{Bi}$ axis direction-component in the local coordinate system $C_{Bi}$ of each geomagnetism will be represented by Equation 8 below.

$$m_{obsi}^t = [M_{Bi\_X}^t\ M_{Bi\_Y}^t\ M_{Bi\_Z}^t]^T \quad (8)$$

Geomagnetism $m^t_{th}$ acquired by correcting the output of each geomagnetic sensor 114-$i$ represented by Equation 8 which rotates around the $X_G$ axis and around the $Y_G$ axis of the global coordinate system $C_G$ is calculated by Equation 9 below, by using each pitch angle $\alpha_i^t$ and each roll angle $\beta_i^t$ acquired in Equations 6 and 7.

$$m_{th}^t = R_{Xi} R_{Yi} m_{obsi}^t \quad (9)$$

$$= \begin{bmatrix} 1 & 0 & 0 \\ 0 & \cos\alpha_i^t & -\sin\alpha_i^t \\ 0 & \sin\alpha_i^t & \cos\alpha_i^t \end{bmatrix} \begin{bmatrix} \cos\beta_i^t & 0 & \sin\beta_i^t \\ 0 & 1 & 0 \\ -\sin\beta_i^t & 0 & \cos\beta_i^t \end{bmatrix} \begin{bmatrix} M_{Bi\_X}^t \\ M_{Bi\_Y}^t \\ M_{Bi\_Z}^t \end{bmatrix}$$

$$= \begin{bmatrix} \cos\beta_i^t & 0 & \sin\beta_i^t \\ \sin\alpha_i^t\sin\beta_i^t & \cos\alpha_i^t & -\sin\alpha_i^t\cos\beta_i^t \\ -\cos\alpha_i^t\sin\beta_i^t & \sin\alpha_i^t & \cos\alpha_i^t\cos\beta_i^t \end{bmatrix} \begin{bmatrix} M_{Bi\_X}^t \\ M_{Bi\_Y}^t \\ M_{Bi\_Z}^t \end{bmatrix}$$

Geomagnetism after correction represented by Equation 9 above will be represented by Equation 10 below.

$$m_{th}^t = [E_{i\_X}^t\ E_{i\_Y}^t\ E_{i\_Z}^t]^T \quad (10)$$

In an equation representing the geomagnetism represented in Equations 9 and 10, in the case of the $X_{Bi}$ axis direction component, the $Y_{Bi}$ axis direction component, and the $Z_{Bi}$ axis direction component of the geomagnetic vector measured by the geomagnetic sensor 114-$i$, only the yaw angle $\gamma_i^t$ rotates with respect the global coordinate system $C_G$ because the pitch angle $\alpha_i^t$ and the roll angle $\beta_i^t$ are corrected. Therefore, an angle $\theta^t_{base\_i}$ at which the sensor unit 110-$i$ forms with respect to magnetic north, that is, the yaw angle $\gamma_i^t$ may be represented by Equation 11 below by using Equation 10.

$$\gamma_i^t = \theta_{base\_i}^t = \tan^{-1}(E_{i\_Y}^t / E_{i\_X}^t) \quad (11)$$

Herein, Equations 12.1 and 12.2 are derived from Equations 9 and 10.

$$E_{i\_X}^t = M_{Bi\_X}^t \cos\beta_i^t + M_{Bi\_Z}^t \sin\beta_i^t \quad (12.1)$$

$$E_{i\_Y}^t = M_{Bi\_Y}^t \cos\alpha_i^t + \sin\alpha_i^t(M_{Bi\_X}^t \sin\beta_i^t - M_{Bi\_Z}^t \cos\beta_i^t) \quad (12.2)$$

Further, in this embodiment, since the $X_G$-axis direction of the global coordinate system $C_G$ is set to coincide with a magnetic north direction, the angle $\theta^t_{base\_i}$ at which the sensor unit 110-$i$ forms with the magnetic north coincides with the yaw angle $\gamma^t_i$, but in the case where the $X_G$-axis direction of the global coordinate system $C_G$ does not coincide with the magnetic north, it is necessary to correct a misalignment thereof. The correction may be easily performed by adding or subtracting the misalignment to or from the formed angle $\theta^t_{base\_i}$.

As such, the rest attitude calculation unit 137 of the shape calculation unit 136 may acquire a pitch angle $\alpha^t_i$, a roll angle $\beta^t_i$, and a yaw angle $\gamma^t_i$ of each sensor unit 110-$i$ at each time t, based on the outputs of the each acceleration sensor 112-$i$ and each geomagnetic sensor 114-$i$.

Figure 6:
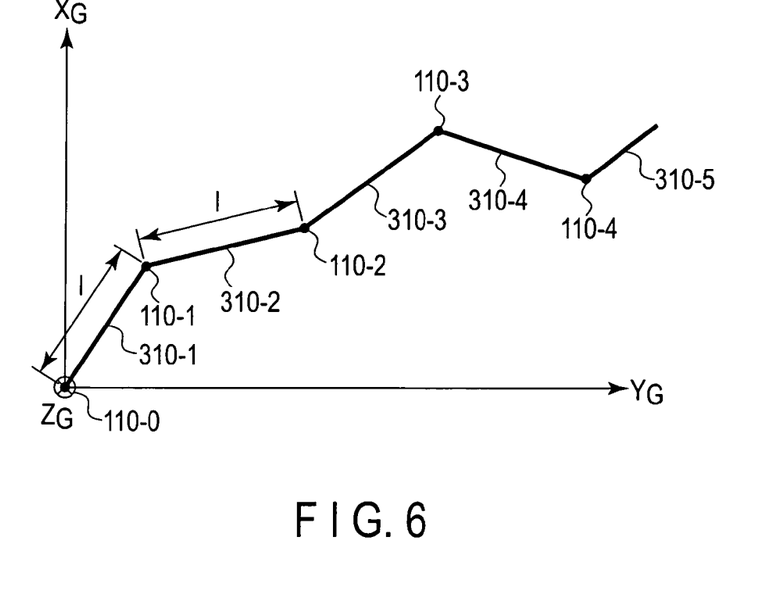
FIG. 6 is a schematic diagram for describing calculation of the shape of the insertion portion.

Referring back to FIG. 5, the description is continued. In step S203, the coordinate calculation unit 138 in the shape calculation unit 136 calculates a coordinate of each sensor unit 110-$i$. A calculation method of the coordinate of each sensor unit 110-$i$ will be described. A schematic diagram of the shape of the insertion portion 210 of the endoscope 200 is illustrated in FIG. 6. As illustrated in FIG. 6, a plurality of links 310 is continuously formed in the insertion portion 210, and the sensor unit 110 is disposed at a connection portion of each link. Herein, a sensor unit 110-($i$−1) is disposed at a proximal end side of a link 310-$i$, and the sensor unit 110-$i$ is disposed at a distal end side of the link 310-$i$. Further, the length of each link 310 is set as an interval l between the sensor units 110.

In this case, when it is assumed that the proximal end of the link 310-$i$ in which the sensor unit 110-($i$−1) is disposed is positioned at the original point of the global coordinate system $C_G$, a coordinate $l^t_i$ of the distal end of the link 310-$i$ where the sensor unit 110-$i$ is disposed is represented by Equation 14 below by using Equation 13 below.

$$e_y = [0\ 1\ 0]^T \quad (13)$$

$$l^t_i = l \cdot C^G_{Bi} \cdot e_y = l \begin{bmatrix} -\sin\gamma^t_i \cdot \cos\alpha^t_i \\ \cos\gamma^t_i \cdot \cos\alpha^t_i \\ \sin\alpha^t_i \end{bmatrix} \quad (14)$$

A coordinate $S^t_i$ of each sensor unit 110-$i$ in the global coordinate system $C_G$ will be represented by Equation 15 below.

$$S^t_i = [L_{Gi\_X}{}^t L_{Gi\_Y}{}^t L_{Gi\_Z}{}^t]^T \quad (15)$$

In this case, the coordinate $S^t_i$ of each sensor unit 110-$i$ is acquired through Equation 16 below by using Equation 14.

$$S^t_i = S^t_{i-1} + l^t_i \quad (16)$$

That is, the coordinate $S^t_i$ of each sensor unit 110-$i$ may be determined sequentially from the proximal end side which is the original point of the global coordinate system $C_G$.

By this configuration, the shape calculation unit 136 may acquire a position and an attitude of each sensor unit 110-$i$ with respect to the global coordinate system $C_G$, based on the outputs of each acceleration sensor 112-$i$ and each geomagnetic sensor 114-$i$. That is, the shape calculation unit 136 may acquire the shape of the insertion portion 210 of the endoscope 200. Thereafter, the shape calculation unit 136 terminates the rest shape calculation processing and the process returns to step S103 by using the position and the attitude of each sensor unit 110-$i$ as a return value. The calculated position and attitude of each sensor unit 110-$i$ are stored in the memory 148 through the control unit 132. When the rest shape calculation processing of step S103 is terminated, the process proceeds to step S110.

In the determination of step S102, when a difference of acceleration is larger than a threshold value, that is, when the insertion portion 210 is in the movement state, the process proceeds to step S104. In step S104, the movement determination unit 133 determines whether the difference of the acceleration is larger than the threshold value. While the difference of the acceleration is larger than the threshold value, that is, while the insertion portion 210 is in the movement state, the movement determination unit 133 repeats the determination of step S104. In the determination of step S104, when the difference of the acceleration is less than or equal to the threshold value, that is, when the insertion portion 210 is in the resting state, the process proceeds to step S105. In step S105, the movement period specification unit 134 specifies a period in the movement state as a movement period.

In step S106, the shape calculation unit 136 performs rest shape calculation processing, with respect to two resting states just before and just after the movement period specified by the movement period specification unit 134. That is, the position and the attitude of each sensor unit 110-$i$ in the global coordinate system $C_G$ are calculated by the rest shape calculation processing described with reference to Equations 1 to 16, with respect to two resting states just before and the just after the movement period. Herein, since the data acquired from each sensor unit 110-$i$ at each time is stored in the memory 148, the stored data may be read and used. Further, since the position and the attitude of each sensor unit 110-$i$ just before the movement period are already calculated in step S103 and thus stored in the memory 148, the position and the attitude may be used. In addition, the position and the attitude of each sensor unit 110-$i$ calculated by the rest shape calculation processing is stored in the memory 148.

In step S107, the movement state estimation unit 142 of the controller 130 performs movement state estimation processing. In the movement state estimation processing, the position and the attitude of each sensor unit 110-$i$ at each time t in the movement state are estimated, and a movement vector indicating a movement direction and a movement amount in the movement state is calculated. The movement state estimation processing will be described with reference to a flowchart illustrated in FIG. 7.

Figure 7:
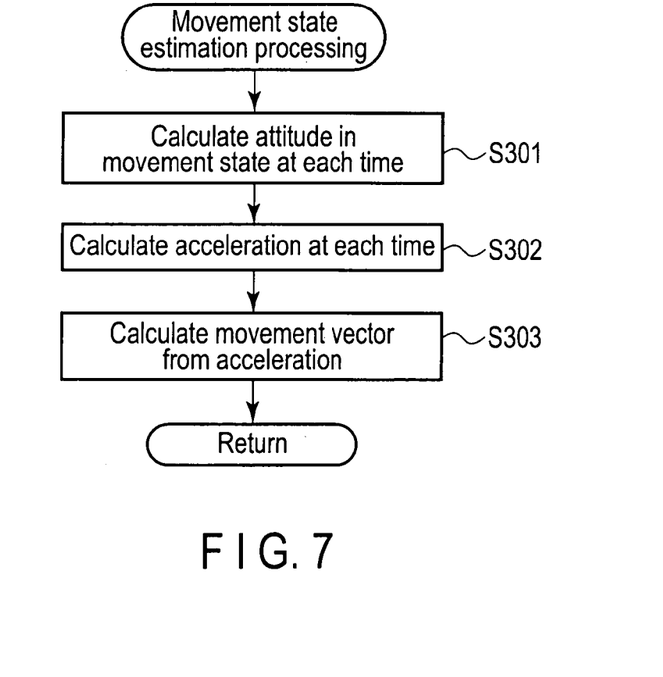
FIG. 7 is a flowchart illustrating a movement state estimation processing of the apparatus for displaying a shape of an insertion portion according to the embodiment of the present invention.

In step S301, the attitude estimation unit 143 in the movement state estimation unit 142 estimates the attitude of each sensor unit 110-$i$ at each time t in the movement state. The estimation of the attitude is based on an attitude at a time t1 which is a movement start time and an attitude at a time t4 which is a movement end time. For example, the attitude at each time t between the time t1 and the time t4 is acquired by linear complementation. That is, the attitude of each sensor unit 110-$i$ in the movement state is acquired by Equation 17 below.

$$\alpha^t_i = \alpha^{t1}_i + \frac{t - t1}{t4 - t1}(\alpha^{t4}_i - \alpha^{t1}_i) \quad (17)$$

$$\beta^t_i = \beta^{t1}_i + \frac{t - t1}{t4 - t1}(\beta^{t4}_i - \beta^{t1}_i)$$

$$\gamma^t_i = \gamma^{t1}_i + \frac{t - t1}{t4 - t1}(\gamma^{t4}_i - \gamma^{t1}_i)$$

Note that, the linear complementation is one example and a complementation method is not limited thereto.

In step S302, the movement vector calculation unit 144 in the movement state estimation unit 142 converts the output of each acceleration sensor 112-$i$ into the acceleration in the global coordinate system $C_G$. The conversion is based on the attitude of each sensor unit 110 at each time in the movement state acquired by Equation 17. That is, the acceleration $a^t_{Gi}$ in the global coordinate system $C_G$ is acquired by Equation 18 below.

$$a_{Gi}^t = C_B^G a_{obsi}^t \qquad (18)$$

$$= \begin{bmatrix} -\sin\gamma_i^t \cdot \sin\alpha_i^t \cdot \sin\beta_i^t + & & \sin\gamma_i^t \cdot \sin\alpha_i^t \cdot \cos\beta_i^t + \\ \cos\beta_i^t \cdot \cos\gamma_i^t & -\sin\gamma_i^t \cdot \cos\alpha_i^t & \sin\beta_i^t \cdot \cos\gamma_i^t \\ \cos\gamma_i^t \cdot \sin\alpha_i^t \cdot \sin\beta_i^t + & & -\cos\gamma_i^t \cdot \sin\alpha_i^t \cdot \cos\beta_i^t + \\ \cos\beta_i^t \cdot \sin\gamma_i^t & \cos\gamma_i^t \cdot \cos\alpha_i^t & \sin\beta_i^t \cdot \sin\gamma_i^t \\ -\cos\alpha_i^t \cdot \sin\beta_i^t & \sin\alpha_i^t & \cos\alpha_i^t \cdot \cos\beta_i^t \end{bmatrix} \cdot \begin{bmatrix} a_{Bi\_X}^t \\ a_{Bi\_Y}^t \\ a_{Bi\_Z}^t \end{bmatrix}$$

$$= \begin{bmatrix} a_{Gi\_X}^t \\ a_{Gi\_Y}^t \\ a_{Gi\_Z}^t \end{bmatrix}$$

Movement acceleration of each sensor unit 110-$i$ is acquired by reducing gravity acceleration from the acceleration $a_{Gi}^t$ in the global coordinate system $C_G$ represented by Equation 18. That is, movement acceleration $a_{Gi\_m}^t$ of each sensor unit 110-$i$ is acquired through Equation 19 below.

$$a_{Gi\_m}^t = a_{Gi}^t - [0 \ 0 \ -g]^T \qquad (19)$$

$$= \begin{bmatrix} a_{Gi\_X}^t \\ a_{Gi\_Y}^t \\ a_{Gi\_Z}^t - g \end{bmatrix}$$

In step S303, the movement vector calculation unit 144 integrates the movement acceleration $a_{Gi\_m}^t$ of each sensor unit 110-$i$ twice to acquire the movement vector. That is, a movement vector $d_{Gi}$ of each sensor unit 110-$i$ in the movement state is acquired through Equation 20 below.

$$d_{Gi} = \sum_{t1}^{t4} \sum_{t1}^{t4} a_{Gi\_m}^t = \begin{bmatrix} d_{Gi\_X} \\ d_{Gi\_Y} \\ d_{Gi\_Z} \end{bmatrix} \qquad (20)$$

By this configuration, the movement state estimation unit 142 may acquire the movement vector $d_{Gi}$ of each sensor unit 110-$i$ during the movement state. The movement state estimation unit 142 terminates the movement state estimation processing, and the process returns to step S107 by using the movement vector $d_{Gi}$ of each sensor unit 110-$i$ as the return value. The movement vector $d_{Gi}$ of each sensor unit 110-$i$ calculated by the movement state estimation processing is stored in the memory 148 through the control unit 132.

Referring back to FIG. 3, the description is continued. In step S108, the image generation unit 146 calculates a coordinate on an image regarding a display vector which is an arrow indicating a movement vector displayed on the display unit 150. First, a magnitude of the display vector is determined by multiplying an appropriate positive coefficient by the movement vector $d_{Gi}$ acquired by Equation 20. That is, a vector r is calculated by Equation 21 below.

$$r = k \begin{bmatrix} d_{Gi\_X} \\ d_{Gi\_Y} \\ d_{Gi\_Z} \end{bmatrix} \qquad (21)$$

In addition, the image generation unit 146 calculates a start point $P_{Gi\_s}$ and an end point $P_{Gi\_e}$ of the display vector by using Equation 22 below, based on the vector r.

$$P_{Gi\_s} = \begin{bmatrix} L_{Gi\_X} \\ L_{Gi\_Y} \\ L_{Gi\_Z} \end{bmatrix} - \left\{ \text{sign} \begin{bmatrix} d_{Gi\_X} \\ d_{Gi\_Y} \\ d_{Gi\_Z} \end{bmatrix} \cdot \text{sqrt}\left( \left\| \begin{bmatrix} d_{Gi\_X} \\ d_{Gi\_Y} \\ d_{Gi\_Z} \end{bmatrix} \right\| \right) + \begin{bmatrix} U_{i\_X} \\ U_{i\_Y} \\ U_{i\_Z} \end{bmatrix} \right\} / M \qquad (22)$$

$$P_{Gi\_e} = \begin{bmatrix} L_{Gi\_X} \\ L_{Gi\_Y} \\ L_{Gi\_Z} \end{bmatrix} + \left\{ \text{sign} \begin{bmatrix} d_{Gi\_X} \\ d_{Gi\_Y} \\ d_{Gi\_Z} \end{bmatrix} \cdot \text{sqrt}\left( \left\| \begin{bmatrix} d_{Gi\_X} \\ d_{Gi\_Y} \\ d_{Gi\_Z} \end{bmatrix} \right\| \right) + \begin{bmatrix} U_{i\_X} \\ U_{i\_Y} \\ U_{i\_Z} \end{bmatrix} \right\} / M$$

Herein, M is an appropriate positive integer. Further, sign is a function which is 1.0 when a variable is greater than or equal to 0 and −1.0 when the variable is smaller than 0. In addition, sqrt is a function which derives a square root of the variable. The square root is acquired to adjust the magnitude of the display vector. If the magnitude may be appropriately adjusted, a used equation is not limited to Equation 22. Further, $U = [U_{i\_X} \ U_{i\_Y} \ U_{i\_Z}]$ in Equation 22 is also added to adjust the magnitude of the display vector.

Further, when $U = [U_{i\_X} \ U_{i\_Y} \ U_{i\_Z}]$ is converted into $U = [1 \ 0 \ 0]^T$ when $d_{Gi\_X} > d_{Gi\_Y}$, and $d_{Gi\_X} > d_{Gi\_Z}$, $U = [0 \ 1 \ 0]^T$ when $d_{Gi\_Y} > d_{Gi\_X}$, and $d_{Gi\_Y} > d_{Gi\_Z}$, $U = [0 \ 0 \ 1]^T$ when $d_{Gi\_Z} > d_{Gi\_X}$, and $d_{Gi\_Z} > d_{Gi\_Y}$, $U = [U_{i\_X} \ U_{i\_Y} \ U_{i\_Z}]$ may be a display vector that emphasizes a direction in which the movement amount is largest.

In step S109, the control unit 132 sets a variable p to a predetermined value P. Herein, the variable p functions as a counter for specifying a period to display the display vector, and the predetermined value P is a value which is proportional to the period to display the display vector. Thereafter, the process proceeds to step S110.

Figure 8:
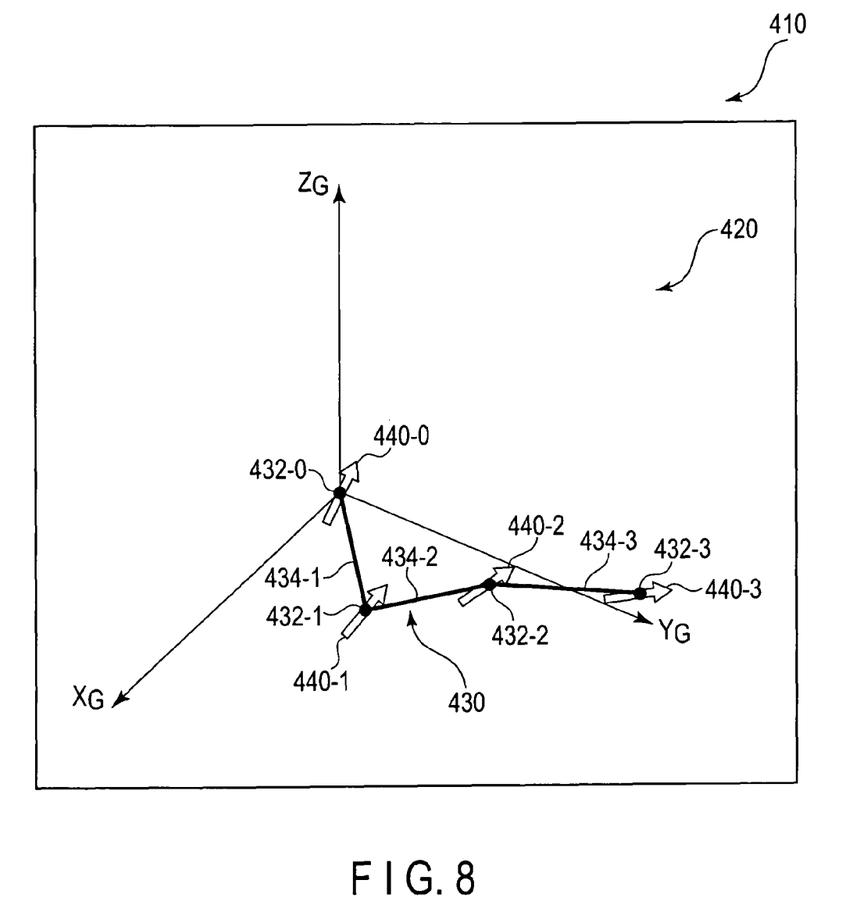
FIG. 8 is a diagram for describing an example of an image displayed in a display unit of the apparatus for displaying a shape of an insertion portion according to the embodiment of the present invention.

In step S110, the image generation unit 146 reads the shape of the insertion portion 210 in the resting state from the memory 148 and displays the read shape on the display unit 150. In an example of the description, the image generation unit 146 displays the shape of the insertion portion 210 calculated in step S103 on the display unit 150 at the time t<t1. The image generation unit 146 displays the shape of the insertion portion 210 just after the movement period calculated in step S106 just after the time t4 and thereafter, displays the shape of the insertion portion 210 calculated in step S103 on the display unit 150 at the time t>t4. For example, as illustrated in FIG. 8, a coordinate system 420 is set and drawn in a display area 410. Next, the position of each sensor unit 110-$i$ is represented by a sensor display sign 432-$i$ in the coordinate system 420 and is connected to a link display sign 434-$i$ to drawn an insertion portion shape 430.

In step S111, the control unit 132 determines whether the variable p is larger than 0. When P is less than or equal to 0, the process proceeds to step S114. Meanwhile, when p is larger than 0, the process proceeds to step S112. In step S112, the image generation unit 146 displays the display vector (for example, an arrow symbol) having a start point $P_{Gi\_s}$ and an end point $P_{Gi\_e}$ calculated by Equation 22 in step S108 as a display vector 440-$i$ at the position of each sensor unit 110-$i$ of the insertion portion shape 430, as illustrated in FIG. 8. In step S113, the control unit 132 sets the variable p as p−1. Thereafter, the process proceeds to step S114.

In step S114, the control unit 132 determines whether the operation of the apparatus for displaying a shape of an insertion portion 100 is terminated. When the operation is not terminated, the process returns to step S101. Meanwhile, when the operation is terminated, the process ends.

By the above processing, when the insertion portion 210 is in the resting state on the coordinate system 420, the shape of the insertion portion 210 is displayed as the insertion portion shape 430 by step S110, in the display unit 150. Meanwhile, until a predetermined time after moving from the movement state to the resting state, that is, until the variable p becomes 0 from P as the counter, the shape of the insertion portion 210 is displayed as the insertion portion shape 430 on the coordinate system 420 and each display vector 440-$i$ in the movement state is displayed to superimpose by step S112.

According to the embodiment, the movement state is displayed on the display unit 150 by an arrow on the display together with the shape of the insertion portion 210. Therefore, a user may verify the shape of the insertion portion 210, and the movement direction and the movement amount through an image while viewing the display. The display supports an operation of the insertion portion 210 by the user.

According to the embodiment, the shape of the insertion portion 210 is displayed every that time based on each acceleration sensor 112-$i$ and each geomagnetic sensor 114-$i$ in the resting state. Further, in the movement state, a movement vector in the corresponding movement state is calculated every that time based on the movement acceleration acquired by correcting the gravity acceleration. In addition, the movement vector in the movement state is displayed for every series of movement states. Therefore, accumulation of errors by continuing integration may be reduced as compared with the shape, the position, and the movement amount of the insertion portion 210 by continuing the integration of the acceleration.

Of course, a diagram illustrated in FIG. 8 is one example illustrating an overview of an image expressing the shape of the insertion portion 210 and the movement vector thereof, and if the image expressing the shape of the insertion portion 210 and the movement vector thereof is illustrated, even any image may be used. For example, the shape of the insertion portion 210 may be displayed to imitate a shape of the endoscope. Further, for example, the movement vector may be represented by moving the diagram illustrating the insertion portion 210 by using animation instead of the display vector 440-$i$. In this case, required information may be calculated by appropriately changing the process of step S108.

Further, in this embodiment, by assuming that the respective sensor units 110-$i$ are connected to each other by linear links 310-$i$, the shape of the insertion portion 210 is calculated, but correction such as connecting the respective sensor units 110-$i$ to each other by a curve line may be appropriately achieved. In addition, in this embodiment, an example in which the apparatus for displaying a shape of an insertion portion is applied to the endoscope, but the apparatus for displaying a shape of an insertion portion may be applied to various apparatuses having an insertion portion which is transformed and inserted, such as a catheter used by passing through the endoscope or other treatment mechanisms.

Further, in estimating the movement acceleration in the movement state, a low-pass filter is applied for the output of the acceleration sensor to estimate the gravity acceleration by reducing an influence of the movement acceleration. In this case, the movement vector may be calculated without estimating the attitude by the linear complementation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for estimating a shape of an insertion portion comprising:
   an insertion portion configured to be transformed;
   an acceleration calculation unit configured to calculate acceleration at each of a plurality of measurement points set in the insertion portion;
   a determination unit configured to determine whether the measurement points move, based on the acceleration calculated by the acceleration calculation unit;
   an attitude information calculation unit configured to calculate first attitude information of each of the measurement points in a resting state before a movement period when the determination unit determines that the measurement points moves and second attitude information of each of the measurement points in a resting state after the movement period;
   an attitude estimation unit configured to estimate a movement period attitude which is an attitude of each of the measurement points during the movement period, based on the first attitude information and the second attitude information calculated by the attitude information calculation unit;
   a movement vector calculation unit configured to correct the acceleration during the movement period calculated by the acceleration calculation unit, based on the movement period attitude of the measurement points estimated by the attitude estimation unit and to calculate a movement vector which indicates a movement direction and a movement amount of each of the measurement points during the movement period, based on the corrected acceleration;
   a position calculation unit configured to calculate a position of each of the measurement points based on the first attitude information or the second attitude information of the measurement points calculated by the attitude information calculation unit; and
   an image generation unit configured to generate and to output a display image expressing the position of each of the measurement points calculated by the position calculation unit and the movement vector calculated by the movement vector calculation unit.

2. The apparatus according to claim 1, wherein
   the attitude information calculation unit is configured to calculate the first attitude information based on the acceleration calculated by the acceleration calculation unit in the resting state before the movement period and to calculate the second attitude information based on the acceleration calculated by the acceleration calculation unit in the resting state after the movement period.

3. The apparatus according to claim 1, wherein
the insertion portion has an elongate shape, and
the plurality of the measurement points is disposed along a longitudinal axis of the insertion portion.

4. The apparatus according to claim 3, wherein
the image generation unit is configured to generate the display image in which a symbol representing the movement vector is superimposed on a position corresponding to each of the measurement points in the display image.

5. The apparatus according to claim 1, wherein
the movement vector calculation unit is configured to calculate movement acceleration at the measurement points, based on the movement period attitude and the acceleration calculated by the acceleration calculation unit during the movement period.

6. The apparatus according to claim 5, wherein
the movement vector calculation unit is configured to convert the acceleration calculated by the acceleration calculation unit during the movement period based on the movement period attitude into acceleration in a global coordinate system and to reduce gravity acceleration from the acceleration in the global coordinate system.

7. The apparatus according to claim 5, wherein
the movement vector calculation unit is configured to calculate the movement vector by integrating the movement acceleration twice.

8. The apparatus according to claim 1, further comprising:
a geomagnetic sensor configured to measure geomagnetism at the measurement points,
wherein the attitude information calculation unit is configured to calculate the first attitude information from the acceleration of the measurement point measured in the resting state before the movement period when it is determined that the measurement points move and the geomagnetism and to calculate the second attitude information from the acceleration of the measurement points measured in the resting state after the movement period and the geomagnetism.

* * * * *